(12) United States Patent
Forrester (10) Patent No.: US 12,137,927 B2
(45) Date of Patent: Nov. 12, 2024

(54) CUTTING GRASPER FOR VALVE LEAFLET LACERATION

(71) Applicant: Matthew Donavon Forrester, Spokane, WA (US)

(72) Inventor: Matthew Donavon Forrester, Spokane, WA (US)

(*) Notice: Subject to any disclaimer, the term of this patent is extended or adjusted under 35 U.S.C. 154(b) by 220 days.

(21) Appl. No.: 17/157,169

(22) Filed: Jan. 25, 2021

(65) Prior Publication Data

US 2022/0233210 A1    Jul. 28, 2022

(51) Int. Cl.
*A61B 17/295* (2006.01)
*A61B 17/00* (2006.01)
*A61B 17/29* (2006.01)

(52) U.S. Cl.
CPC .. *A61B 17/295* (2013.01); *A61B 2017/00243* (2013.01); *A61B 2017/00353* (2013.01); *A61B 2017/00778* (2013.01); *A61B 2017/2901* (2013.01); *A61B 2017/2905* (2013.01); *A61B 17/2909* (2013.01); *A61B 2017/2927* (2013.01);

(Continued)

(58) Field of Classification Search
CPC .............. A61B 17/295; A61B 17/2909; A61B 2017/00243; A61B 2017/00353; A61B 2017/00778; A61B 2017/2901; A61B 2017/2905; A61B 2017/2927; A61B 2017/2932; A61B 2017/2947; A61B 17/3201; A61B 17/320016; A61B 2017/22097; A61B 2017/320064; A61B 2017/2929

See application file for complete search history.

(56) References Cited

U.S. PATENT DOCUMENTS 5,514,157 A * 5/1996 Nicholas ............ A61B 17/0218
                                                                606/198
5,584,842 A  12/1996 Fogarty et al.
(Continued)

FOREIGN PATENT DOCUMENTS

WO    2007067556    6/2007

OTHER PUBLICATIONS

"International Search Report and Written Opinion", PCT Application No. PCT/US22/12280, Apr. 1, 2022, 9 pages.
(Continued)

*Primary Examiner* — Kathleen S Holwerda
*Assistant Examiner* — Serenity A Miller
(74) *Attorney, Agent, or Firm* — FIG. 1 Patents (57) ABSTRACT

A cutting grasper for valve leaflet laceration is described. The cutting grasper extends from a distal end of a flexible shaft so that the flexible shaft is configured to advance the cutting grasper through a vascular system of a patient. The cutting grasper includes a base member having a proximal end that is attached to the distal end of the flexible shaft. The cutting grasper also includes an actuating member. A proximal end of the actuating member is rotatably attached to the distal end of the base member forming a hinge of the cutting grasper. The actuating member is configured to rotate relative to the base member about the hinge between open and closed positions. The cutting grasper is configured to grasp a target leaflet in the open position, close into the closed position with the target leaflet disposed between the base and actuating members, and divide the target leaflet.

14 Claims, 11 Drawing Sheets

(52) U.S. Cl.
CPC ............... *A61B 2017/2932* (2013.01); *A61B 2017/2947* (2013.01)

(56) References Cited

U.S. PATENT DOCUMENTS

| | | | | |
|---|---|---|---|---|
| 5,792,135 | A * | 8/1998 | Madhani | A61B 34/77 606/1 |
| 11,013,527 | B1 * | 5/2021 | Podmore | A61B 17/320016 |
| 11,234,716 | B2 * | 2/2022 | Kahmer | A61B 17/1671 |
| 2003/0236549 | A1 * | 12/2003 | Bonadio | A61B 17/28 606/205 |
| 2008/0312652 | A1 * | 12/2008 | Bell | A61B 18/1445 606/51 |
| 2009/0209955 | A1 | 8/2009 | Forster et al. | |
| 2013/0165907 | A1 * | 6/2013 | Attar | A61B 17/3201 606/1 |
| 2013/0325048 | A1 * | 12/2013 | Weiman | A61B 17/025 606/1 |
| 2014/0378998 | A1 | 12/2014 | Rizzuto et al. | |
| 2018/0000473 | A1 * | 1/2018 | Pasquino | A61B 17/072 |
| 2018/0092661 | A1 | 4/2018 | Prabhu | |
| 2019/0029790 | A1 * | 1/2019 | Bak-Boychuk | A61F 2/013 |
| 2019/0336157 | A1 * | 11/2019 | Ahrens | A61B 17/1608 |
| 2021/0346045 | A1 * | 11/2021 | Abunassar | A61M 25/0147 |
| 2021/0346081 | A1 * | 11/2021 | Childs | A61B 17/320016 |

OTHER PUBLICATIONS

Khan, Jaffar et al., "Anterior Leaflet Laceration to Prevent Ventricular Outflow Tract Obstruction During Transcatheter Mitral Valve Replacement", Journal of the American College of Cardiology, vol. 73, Issue 20, published by Elsevier on behalf of the American College of Cardiology [retrieved Aug. 31, 2020]. Retrieved from the Internet <https://doi.org/10.1016/j.jacc.2019.02.076>., May 28, 2019, 14 pages.

Testa, Luca et al., "Transcatheter Mitral Valve Replacement in the Transcatheter Aortic Valve Replacement Era", Journal of the American Heart Association [retrieved Aug. 31, 2020]. Retrieved from the Internet <https://www.ahajournals.org/doi/10.1161/JAHA.119.013352>., Nov. 19, 2019, 11 pages.

\* cited by examiner

CUTTING GRASPER FOR VALVE LEAFLET LACERATION

BACKGROUND

Millions of people each year are diagnosed with heart valve disease, the most commonly diseased valves being the aortic and mitral valves. If left untreated, valve disease can lead to life-altering symptoms, congestive heart failure, and death. Often medical management is insufficient, and many patients require surgical intervention such as valve replacement or repair. Some patients are candidates for minimally invasive procedures such as transcatheter mitral valve replacement (TMVR).

TMVR can be complicated by left ventricular outflow tract (LVOT) obstruction. This can occur when a transcatheter mitral valve pushes the anterior leaflet into the left ventricular outflow tract significantly limiting the outflow through the LVOT and aortic valve, which can be fatal. Concerning anatomy for LVOT obstruction is one of the primary reasons that a patient may be denied a transcatheter mitral valve replacement.

To reduce the risk of LVOT obstruction, medical practitioners have developed techniques that involve lacerating the anterior leaflet of the mitral valve, so that when a transcatheter replacement valve is inserted, the leaflet does not obstruct the LVOT. One conventional technique for lacerating the anterior leaflet of the mitral valve concomitantly with mitral valve replacement is the LAMPOON procedure. This procedure requires the use of two transfemoral guide catheters, which are advanced retrograde through the aortic valve and positioned in the LVOT and the left atrium, respectively. An electrified guide wire is advanced through the catheter in the LVOT and is used to perforate the base of the anterior leaflet. It is then snared through the other catheter in the left atrium. Once the guidewire has been successfully snared, tension is applied, and the guide wire is electrified once again to lacerate the anterior leaflet. The wires are then retracted through the LVOT.

This procedure is technically difficult and requires significant operator experience. Accordingly, the LAMPOON procedure is not commonly performed. Additionally, the LAMPOON procedure carries an inherent risk such as inadvertently injuring other anatomical structures. Due to the complexities and risks of such conventional techniques, LVOT obstruction by the anterior leaflet remains a significant barrier to TMVR. Often, there are no alternative treatments, and thus patients are left untreated.

SUMMARY

To minimize LVOT obstruction during TMVR, a percutaneous cutting grasper for valve leaflet laceration is deployed. In one or more implementations, a device includes a flexible shaft and a cutting grasper. The cutting grasper extends from a distal end of the flexible shaft, which is configured to advance the cutting grasper through a vascular system of a patient and into a chamber of the patient's heart. The device can be used to target a valve leaflet, e.g., an anterior leaflet of the patient's mitral valve. The cutting grasper includes a base member having a proximal end that is attached to the distal end of the flexible shaft. The cutting grasper also includes an actuating member. A proximal end of the actuating member is rotatably attached to the distal end of the base member forming a hinge of the cutting grasper. The actuating member is configured to rotate relative to the base member about the hinge between open and closed positions of the cutting grasper. In operation, the cutting grasper is controlled to grasp a target leaflet (e.g., the anterior leaflet of the mitral valve) in the open position, close into the closed position with the target leaflet disposed between the base and actuating members, and then divide the target leaflet while disposed between the base and actuating members.

This Summary introduces a selection of concepts in a simplified form that are further described below in the Detailed Description. As such, this Summary is not intended to identify essential features of the claimed subject matter, nor is it intended to be used as an aid in determining the scope of the claimed subject matter.

BRIEF DESCRIPTION OF THE DRAWINGS

The detailed description is described with reference to the accompanying figures.

DETAILED DESCRIPTION

Overview

Transcatheter mitral valve replacement (TMVR) is a minimally invasive procedure, which may be used for heart valve replacement or repair. However, TMVR can be complicated by left ventricular outflow tract (LVOT) obstruction. This can occur when a transcatheter mitral valve pushes the anterior leaflet into the left ventricular outflow tract significantly limiting the outflow through the LVOT and aortic valve, which can be fatal. Accordingly, medical practitioners have developed techniques that involve intentionally lacerating the anterior leaflet of the mitral valve, so that when a replacement valve is inserted, the leaflet does not obstruct the LVOT.

One conventional approach for laceration of the anterior leaflet of the mitral valve, to prevent LVOT obstruction, is the LAMPOON procedure. This procedure is technically difficult and requires significant operator experience. Additionally, the LAMPOON procedure carries an inherent risk such as inadvertently injuring other anatomical structures. Due to the complexities and risks of such conventional techniques, LVOT obstruction by the anterior leaflet remains a significant barrier to TMVR. Often, there are no alternative treatments, and thus patients are left untreated.

To overcome these problems, a percutaneous cutting grasper for valve leaflet laceration may be deployed. The percutaneous cutting grasper includes a base member having base proximal and distal ends. This cutting grasper also includes an actuating member, which is attached to the distal end of the base member. The junction of the base member and the actuating member forms a hinge of the cutting grasper, and the actuating member is configured to rotate relative to the base member about the hinge. In this way, the cutting grasper may be disposed in and also between open and closed positions, as described in more detail below.

In accordance with the described techniques, the cutting grasper may be attached to a distal end of a flexible shaft that is configured to advance the cutting grasper through a vascular system of a patient, e.g., a person or some other animal. In some scenarios, for example, the flexible shaft can advance the cutting grasper from a femoral vein accessed through an incision in the groin, through the inferior vena cava, to the right atrium of a patient's heart. Following a transeptal puncture, the flexible shaft can further advance the cutting grasper to the left atrium. From there, the flexible shaft can further advance the cutting grasper through the mitral valve and into the left ventricle. This singular catheterized deployment of the cutting grasper in an antegrade direction overcomes limitations of conventional techniques that involve complicated deployment of medical devices, such as the deployment of two separate catheters as part of performing the LAMPOON procedure.

In operation, once the cutting grasper is advanced by the flexible shaft to a desired position, such as disposed in the left ventricle just inferior to the mitral valve, the actuating member rotates into an open position. In one or more implementations, the cutting grasper can be configured to open into the open position automatically responsive to entry into the chamber. Alternatively or in addition, the cutting grasper can be controlled to open into the open position by a user of the device, e.g., a surgeon handling one or more controls communicably coupled to a proximal end of the flexible shaft. While disposed in the open position, the cutting grasper can be retracted towards a target leaflet, e.g., the anterior leaflet of the mitral valve, so that the actuating member is positioned on a ventricular side of the leaflet and the base member is positioned on an atrial side of the leaflet. With the target leaflet disposed between the base and actuating members, one or more grasper closing components may close the cutting grasper into a closed position and secure the target leaflet between the base member and the actuating member.

By way of example, the grasper closing components can include, or otherwise be implemented using, rare earth magnets to draw the members together and securely grasp the leaflet. Additionally or alternatively, the grasper closing components may comprise a system of wires and pulleys. In one or more implementations, the grasper closing components may be configured with a release mechanism which is operable to release the actuating member from the base member. In this way, the cutting grasper can be repositioned, enabling an alignment of the laceration to be adjusted based on the anatomy of the patient. In other words, the cutting grasper is not prevented from being positioned to accurately grasp a target portion of the anterior leaflet of the mitral valve, regardless of an anatomy of the patient.

With the target leaflet grasped between the base and actuating members, the cutting grasper is operable to divide the target leaflet. The target leaflet can be divided by cutting it using one or more lacerating components of the cutting grasper, including, for example, an electrified wire, one or more magnets, and/or one or more blades, to name just a few. Such lacerating components may be located on either or both the base member and the actuating member. In one or more implementations, the lacerating components may include a mechanism to remain idle until the target leaflet is securely grasped by the cutting grasper. In this way, the cutting grasper can mitigate the likelihood of inadvertently damaging healthy tissue. Once the target leaflet is cut, the cutting grasper can be retracted, e.g., by retracting the flexible shaft back through the patient. Additionally, once the target leaflet is cut, the valve is suitably prepared for replacement with minimized risk of LVOT obstruction.

In the following discussion, an example device is described that is configured to employ the techniques described herein. Any reference or depiction of anatomical features in this Application are not necessarily drawn to scale and are not necessarily anatomically accurate, but rather are drawn to illustrate the described device and techniques using the device.

Example Device

Figure 1:
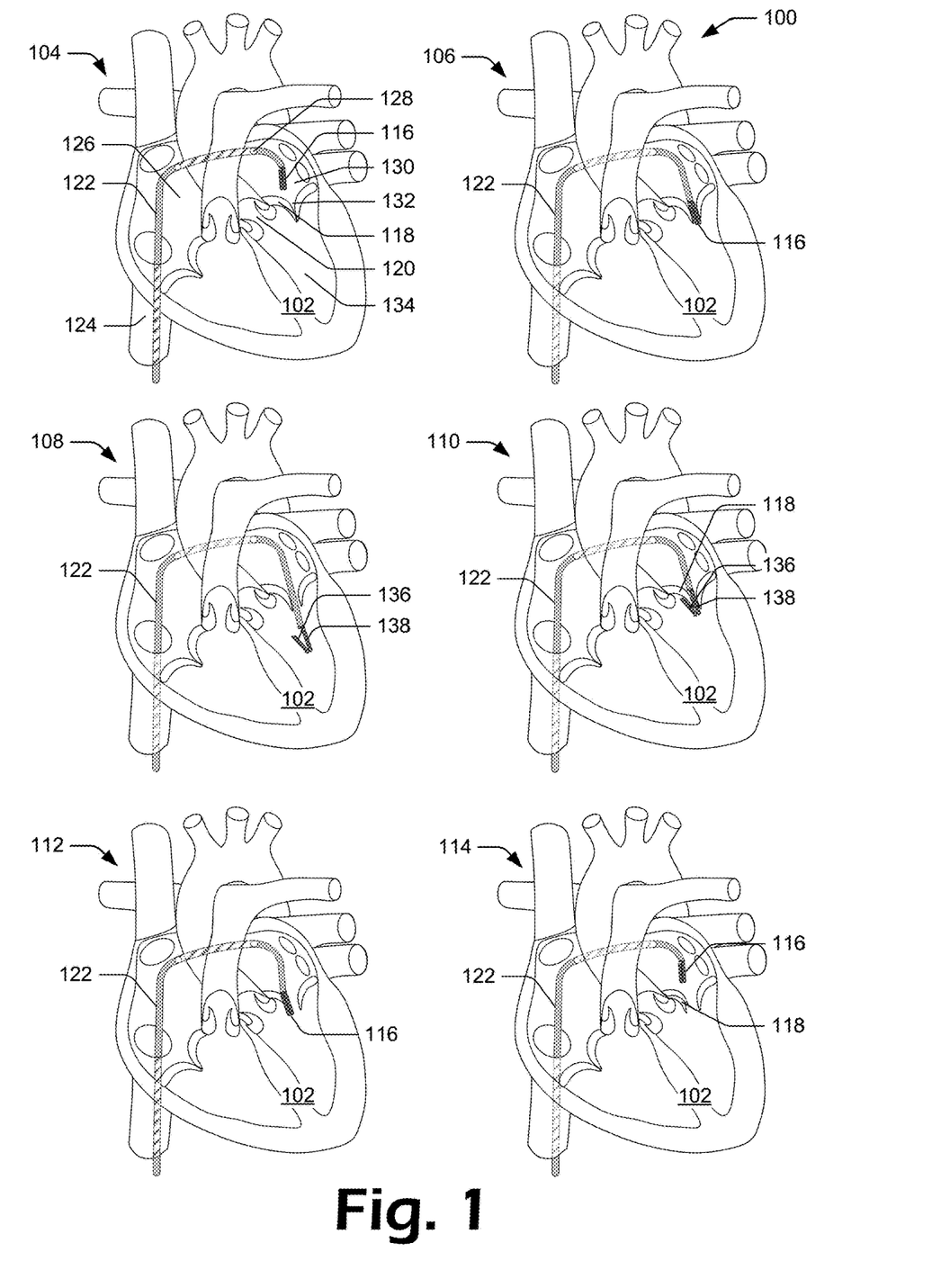
FIG. 1 depicts an example of the cutting grasper in use in an example environment.

FIG. 1 depicts an example 100 of a heart 102 at different stages 104-114 and in which cutting grasper 116 is operated to divide an anterior leaflet 118 of the heart 102's mitral valve. The heart 102 includes left ventricular outflow tract (LVOT 120), relative to which subsequent transcatheter mitral valve replacement surgery may be performed.

In the illustrated example 100, the cutting grasper 116 is attached to a flexible shaft 122 having proximal and distal ends. The cutting grasper 116 extends from the shaft distal end so that the flexible shaft 122 can advance the cutting grasper 116 through a vascular system of a patient. For instance, as depicted in first stage 104 the flexible shaft 122 is configured to advance the cutting grasper 116 through inferior vena cava 124 and into right atrium 126. The flexible shaft 122 further advances the cutting grasper 116 through a transeptal puncture 128 into left atrium 130.

As shown in second stage 106, the cutting grasper 116 is then advanced through mitral valve 132. In general, the mitral valve 132 includes two leaflets, one of which is the anterior leaflet 118. While in left ventricle 134, an actuating member 136 of the cutting grasper 116 may be actuated to rotate relative to a base member 138 of the cutting grasper 116 into an open position as shown in third stage 108, e.g., once the cutting grasper 116 has advanced past the mitral valve 132 and into the left ventricle 134. In operation, the cutting grasper 116 may be retracted while in the open position so that the actuating member 136 is positioned on the ventricular side of the anterior leaflet 118 and so that the base member 138 is positioned on the atrial side, as shown in fourth stage 110.

Based on the anterior leaflet 118 being disposed between the actuating member 136 and the base member 138, the cutting grasper 116 may be said to "grasp" the anterior leaflet 118. The actuating member 136 and the base member 138 are further configured to close against the anterior leaflet 118 as depicted in fifth stage 112. In particular, the actuating member 136 and the base member 138 may be closed against the anterior leaflet 118 by one or more grasper closing components. In accordance with the described techniques, the cutting grasper 116 is operable to divide the anterior leaflet 118 while the anterior leaflet 118 is disposed between the actuating member 136 and the base member 138, such as by using one or more lacerating components. Sixth stage 114 shows the cutting grasper 116 retracting into the left atrium 130, e.g., after the anterior leaflet 118 has been successfully divided such that the anterior leaflet 118 is bisected.

Figure 2:
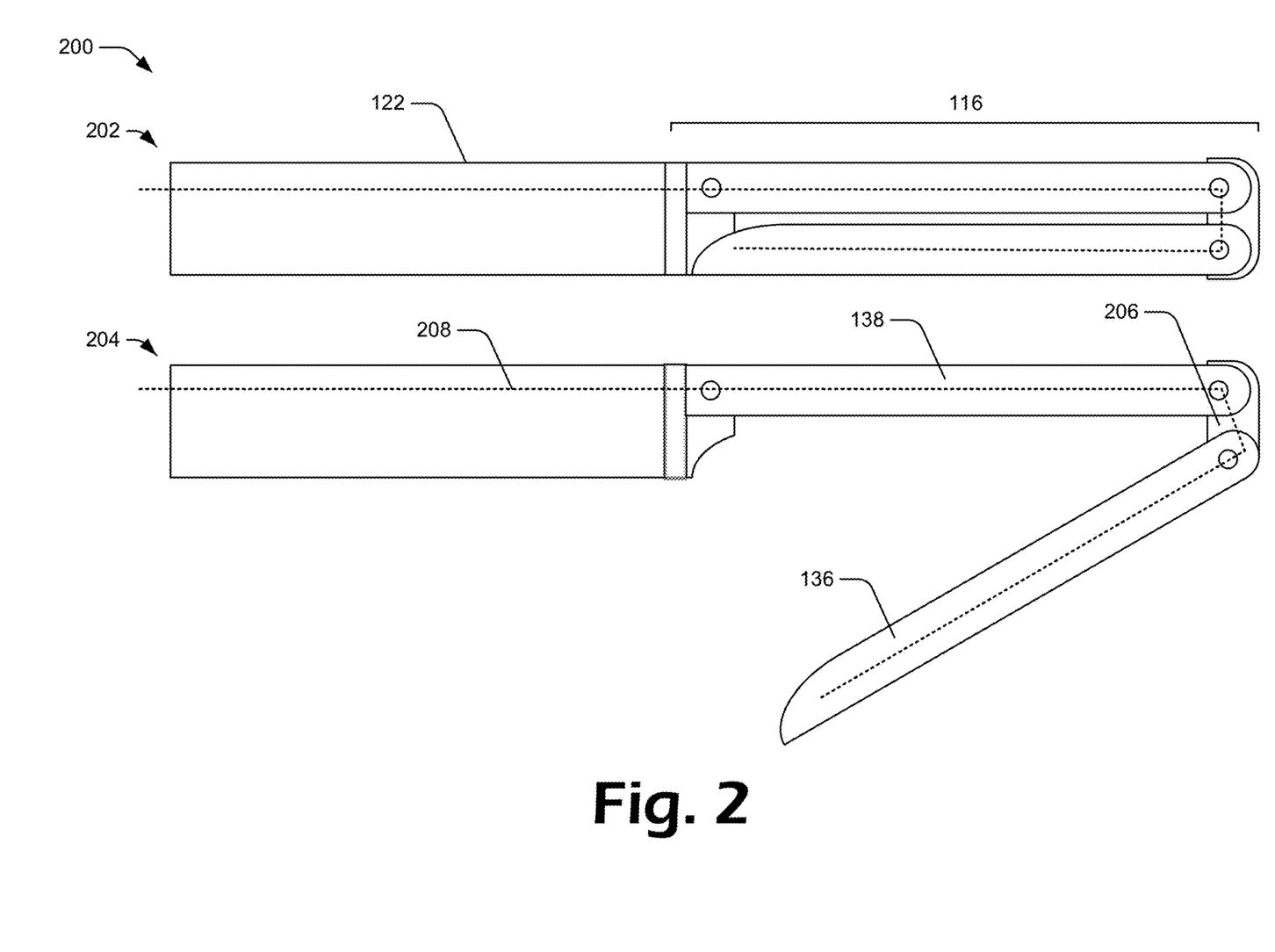
FIG. 2 depicts examples of the cutting grasper in a closed configuration and in an open configuration.

FIG. 2 depicts examples 200 of the cutting grasper 116 in both a closed position 202 and an open position 204. The cutting grasper 116 extends from the distal end of the flexible shaft 122. The flexible shaft 122 may be configured to have a variety of sizes or thicknesses, depending on the desired application or the particular anatomy of the patient without departing from the spirit or scope of the described techniques. Here, the cutting grasper 116 is depicted in more detail with the base member 138, which has proximal and distal ends. In this example, the proximal end of the base member 138 is attached to the distal end of the flexible shaft 122. The actuating member 136, which has proximal and distal ends, is also depicted in the illustrated example 200. In this example 200, the proximal end of the actuating member 136 is rotatably attached at the distal end of the base member 138 forming a hinge 206 of the cutting grasper 116.

The actuating member 136 is configured to rotate relative to the base member 138 about the hinge 206 between the closed position 202 and the open position 204. In this way, the cutting grasper 116 may be disposed in and also between (e.g., at angles between) the open position 204 and the closed position 202. In one more implementations, the cutting grasper 116 is advanced through the vasculature of a patient by the flexible shaft 122 while in the closed position 202. The actuating member 136 may be configured to rotate, causing the cutting grasper 116 to be disposed in the open position 204, automatically, such as in response to entry into a desired heart chamber. Alternatively or additionally, the actuating member 136 can be controlled to cause the cutting grasper 116 to be disposed in the open position 204 by a user of the device, e.g., a surgeon. As noted above, the cutting grasper 116 and or the flexible shaft 122 may be coupled to one or more controls that enable a surgeon to control the flexible shaft 122 and the cutting grasper 116. Similarly, the actuating member 136 can be configured to rotate so that the cutting grasper 116 is disposed in the closed position 202 automatically, such as responsive to a targeted leaflet becoming disposed between the base member 138 and the actuating member 136. Alternatively or additionally, the cutting grasper 116 may be controlled to close into the closed position 202 by a user of the device, e.g., a surgeon.

The cutting grasper 116 may also include one or more grasper closing components that are configured to close the cutting grasper 116 into the closed position 202. In one or more implementations, the grasper closing components may be configured as a system of wires and pulleys 208 as depicted in the illustrated example 200. Additionally or alternatively, the grasper closing components can include, or otherwise be implemented using rare earth magnets to draw the members together. Grasper closing components may include a variety of mechanisms and/or or configured in a variety of ways to close the cutting grasper 116 into the closed position in the spirit and scope of the described techniques.

In one or more implementations, the grasper closing components may be configured with a release mechanism, which is operable to release the actuating member 136 from the base member 138, e.g., returning the cutting grasper to the open position 204. In this way, the cutting grasper 116 can be repositioned into a different position before cutting target tissue.

In accordance with the described techniques, the cutting grasper 116 includes one or more lacerating components to divide targeted tissue. Examples of such lacerating components include, but are not limited to, one or more electrified wires and one or more blades, to name just a few. The lacerating components can be disposed on or within either or both of the base member 138 and/or the actuating member 136. Additionally or alternatively, the lacerating components may be configured so that they remain idle until a target leaflet is disposed between the base member 138 and the actuating member 136. In this way, the cutting grasper 116 can mitigate the risk of accidentally damaging healthy tissue.

Figure 3:
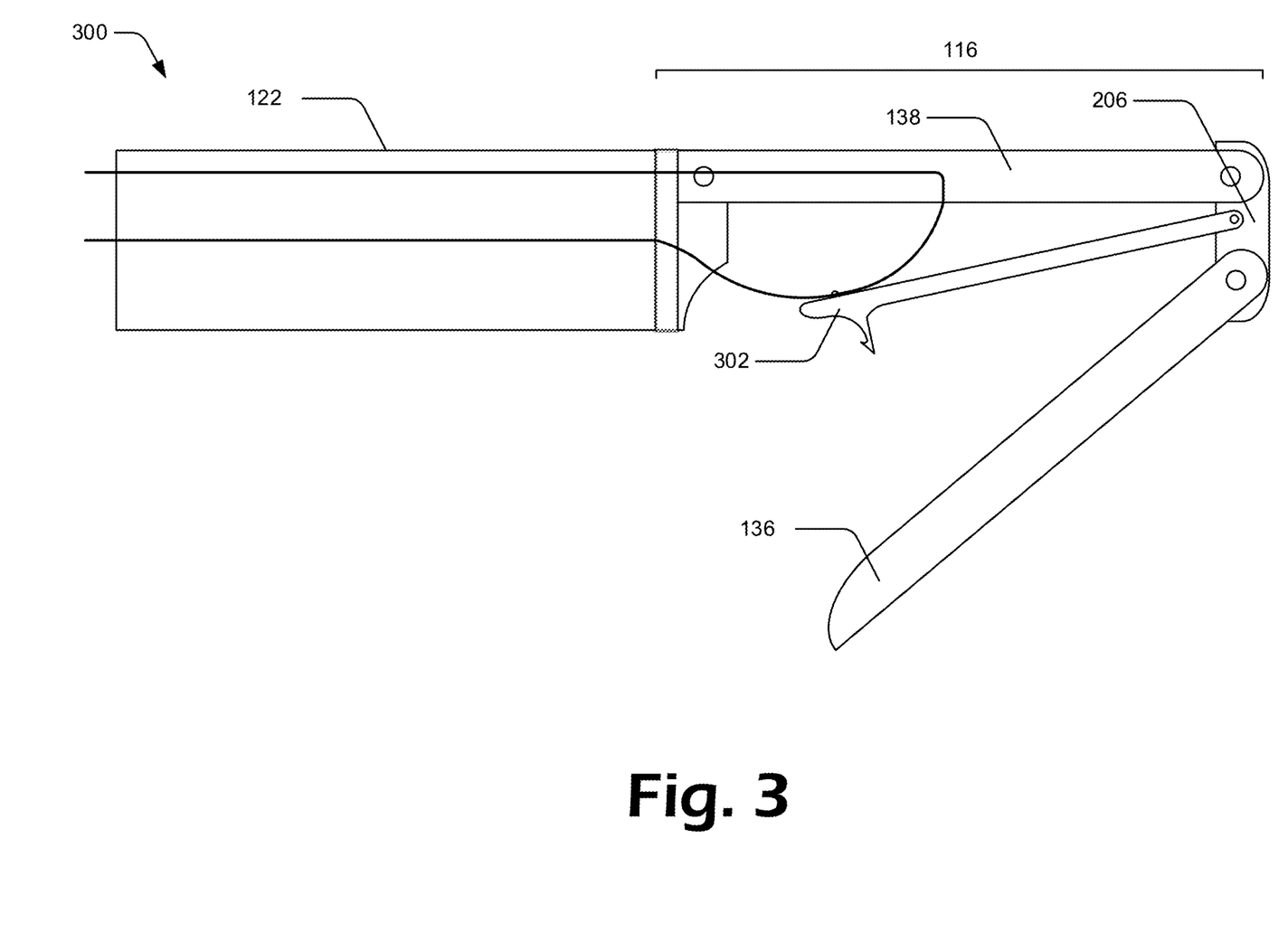
FIG. 3 depicts an example of an alternative implementation in which the cutting grasper includes an independent anchor component.

FIG. 3 depicts an example 300 of an alternative implementation of the cutting grasper 116. In addition to the base member 138 and the actuating member 136, the cutting grasper 116 includes an anchor component 302 in the illustrated example 300. The anchor component 302 is depicted as being attached to the hinge 206 of the cutting grasper 116. Alternatively or additionally, the anchor component 302 may be attached to the distal end of the flexible shaft 122. When the target tissue is disposed between the base member 138 and the actuating member 136, the anchor component 302 may be configured to rotate about the hinge 206 and bind to the actuating member, as a mechanical clasp. Operation of the anchor component 302 in this way can help secure the target tissue between the base member 138 and the actuating member 136. Due to securing the target tissue, the anchor component 302 can ensure the target tissue is disposed within the cutting grasper 116 so that the tissue is divided at an intended location. In one or more implementations, the anchor component 302 may also be configured with a release mechanism, which is operable to release the anchor component 302 from the actuating member 136. In this way, the cutting grasper 116 can be repositioned into a preferred orientation before cutting the target tissue. It is to be appreciated that an anchor component may not be used in one or more implementations, but that the cutting grasper 116 is nevertheless configured to suitably secure the target tissue between the actuating member 136 and the base member 138, e.g., based on the actuating member 136 and the base member 138 closing with suitable force on the target tissue while in the closed position 202. In implementations without the anchor component 302, the cutting grasper 116 may therefore also enable the targeted tissue to be divided at an intended location.

Figure 4:
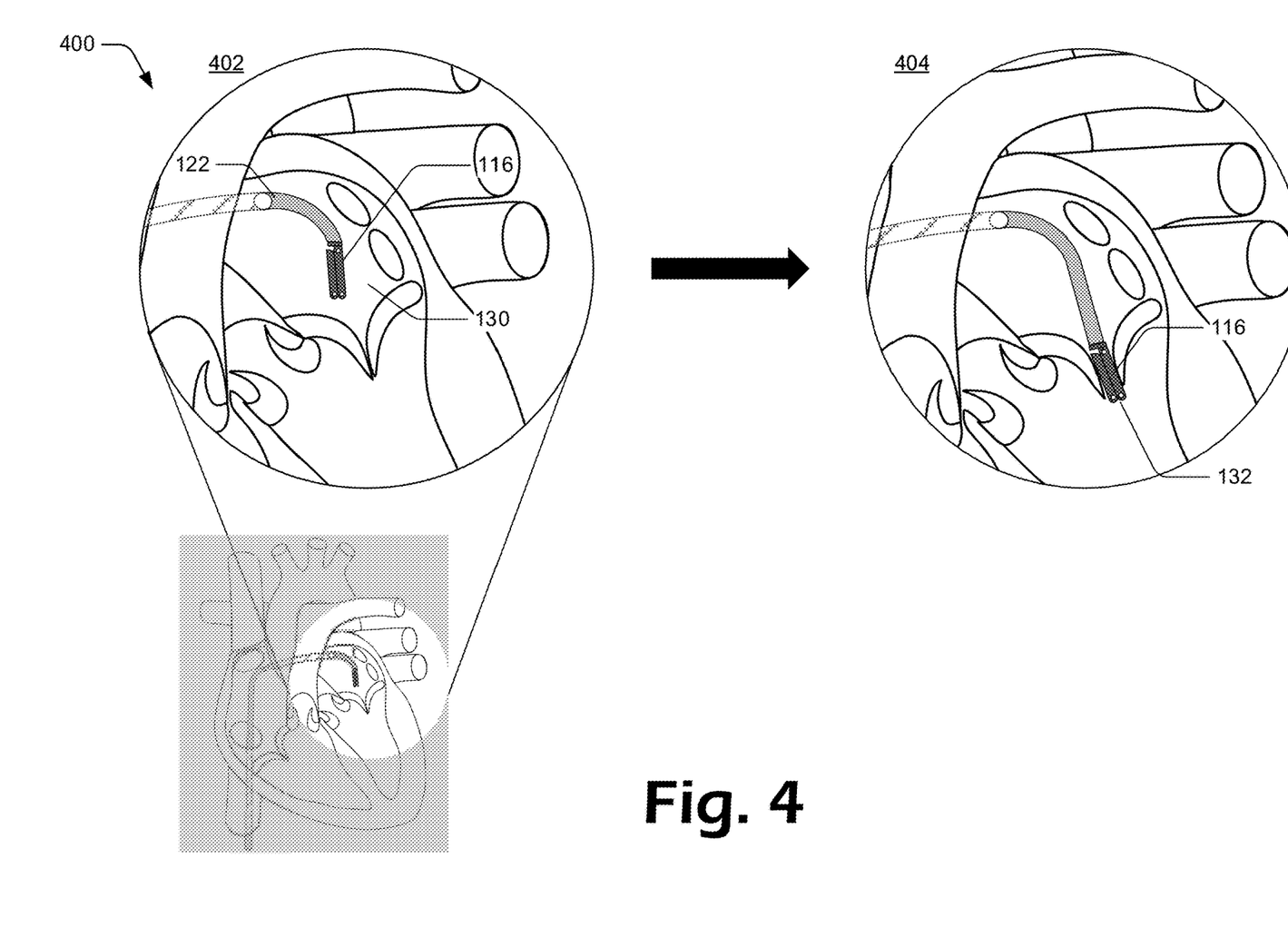
FIG. 4 depicts an example in which the cutting grasper advances from a left atrium to a mitral valve.

FIG. 4 depicts an example 400 in which the cutting grasper 116 is advanced from the left atrium 130 to the mitral valve 132. This advancement is depicted in the illustrated example 400 in detail via first stage 402 and second stage 404.

The first stage 402 depicts the cutting grasper 116 in the closed position 202 while disposed in the left atrium 130. In this example, the flexible shaft 122 is depicted advancing the cutting grasper 116 from the left atrium 130 to the mitral valve 132, as shown in the second stage 404. In one or more implementations, the cutting grasper 116 may be configured to remain in the closed position 202 while being advanced by the flexible shaft 122. This enables the device to move efficiently through vasculature of a patient.

Figure 5:
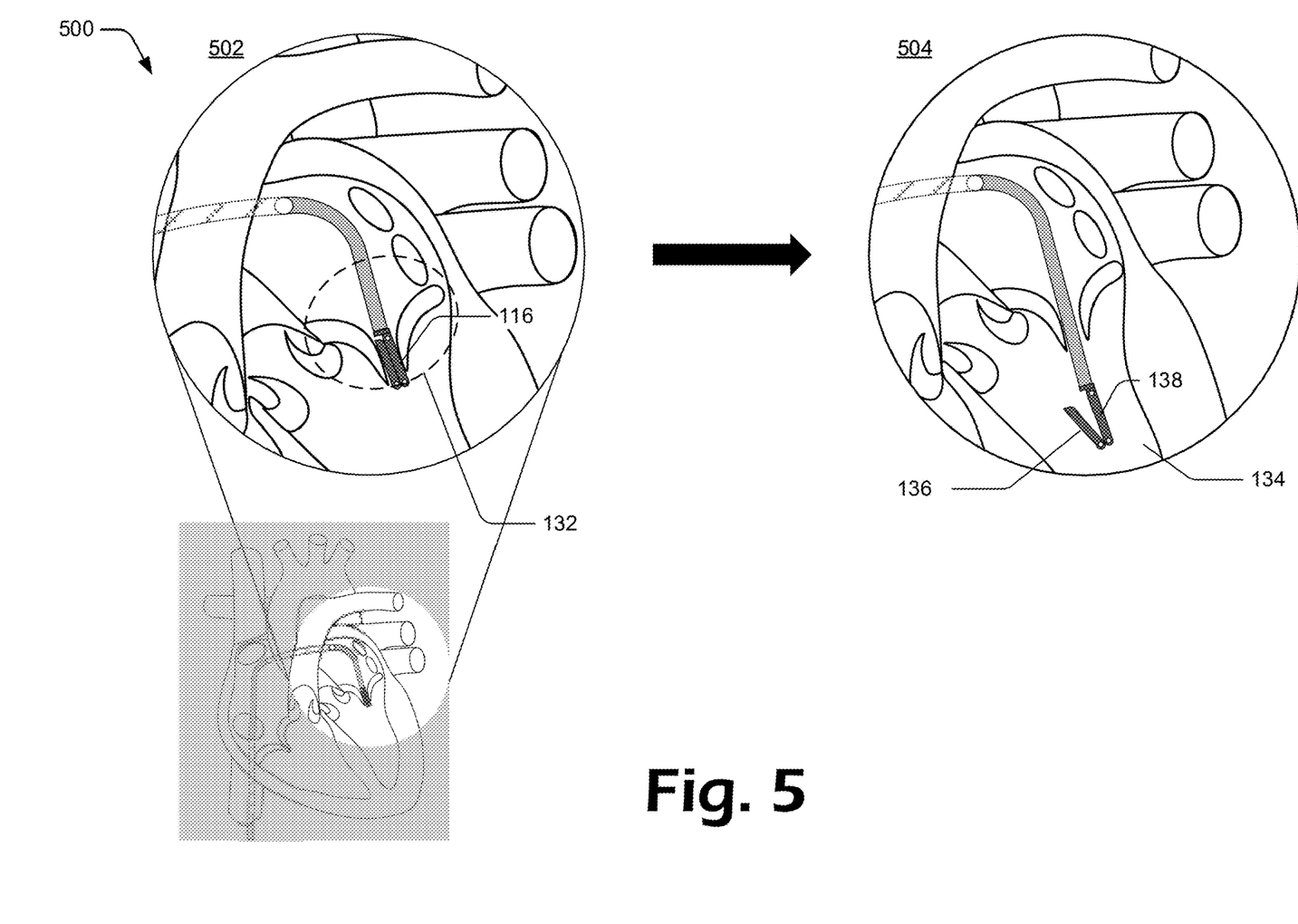
FIG. 5 depicts an example in which the cutting grasper enters a left ventricle and opens into an open position.

FIG. 5 depicts an example 500 in which the cutting grasper 116 is advanced from a position within the mitral valve 132 and into the left ventricle 134. This advancement is depicted in the illustrated example 500 in detail via first stage 502 and second stage 504.

As noted above, the actuating member 136 is configured to rotate about the hinge 206 into the open position 204, such as based on the cutting grasper 116 entering the left ventricle 134. In one or more implementations, the actuating member 136 may "spring" into the open position 204 responsive to entry into the left ventricle 134. This may occur when the cutting grasper 116 is biased in the open position 204 and when the cutting grasper 116 requires force to overcome such biasing to be disposed in the closed position 202. Additionally or alternatively, the cutting grasper 116 can be controlled to open by a user of the device, i.e., a surgeon.

Figure 6:
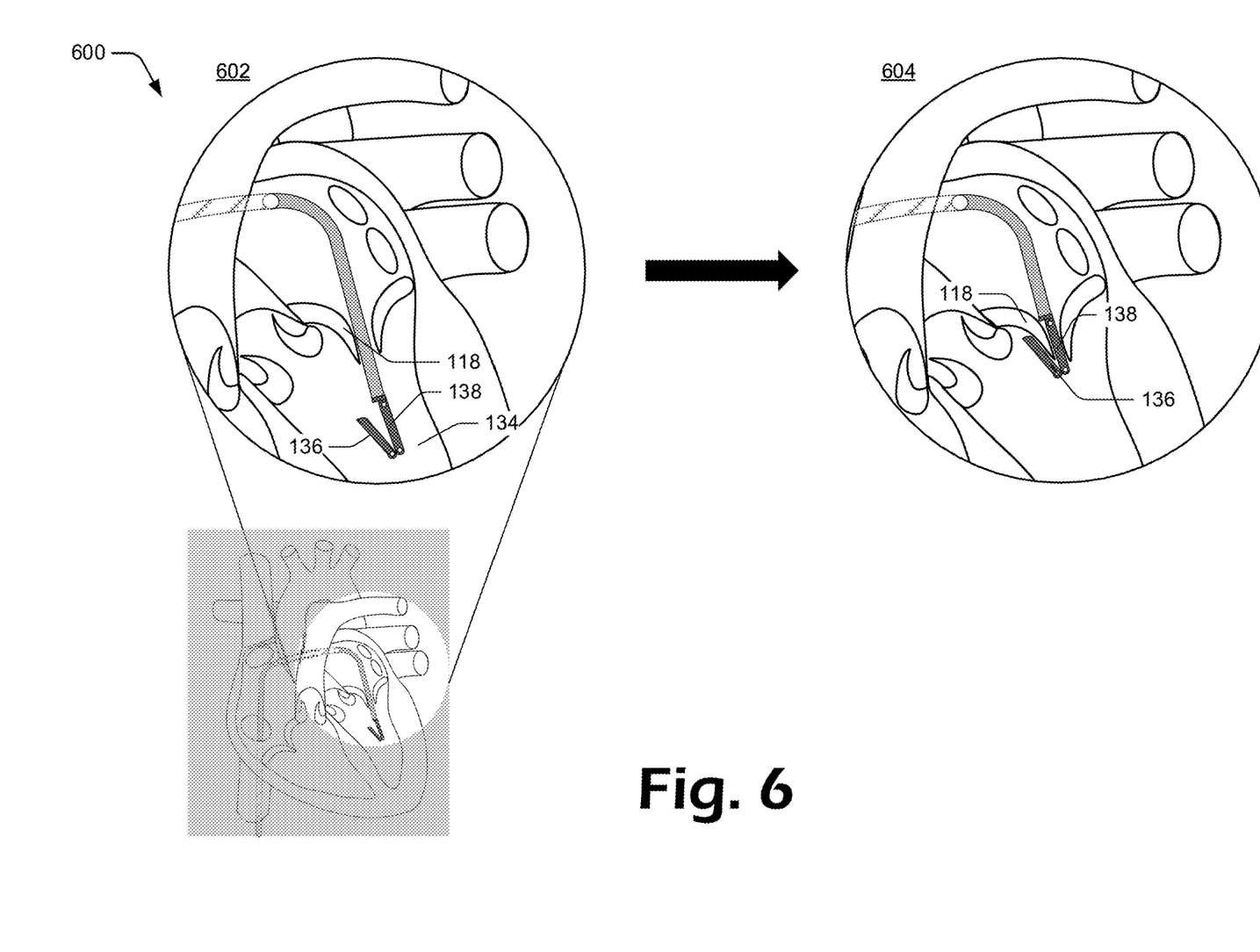
FIG. 6 depicts an example in which the cutting grasper retracts so that an anterior leaflet of a mitral valve is disposed between a base member and an actuating member of the cutting grasper.

FIG. 6 depicts an example 600 in which the cutting grasper 116 is retracted while disposed in the open position 204 from an advanced position in the left ventricle 134 to make contact with the anterior leaflet 118 of the mitral valve 132. This retraction is depicted in detail in the illustrated example 600 via a first stage 602 and a second stage 604. At the second stage 604, the actuating member 136 is depicted positioned on the ventricular side of the anterior leaflet 118 and the base member 138 is depicted positioned on the atrial side of the leaflet. In one or more implementations, the angle between the base member 138 and the actuating member 136 can be adjusted to better contact the anterior leaflet 118, for instance, as controlled by a user of the device, i.e., a surgeon.

Figure 7:
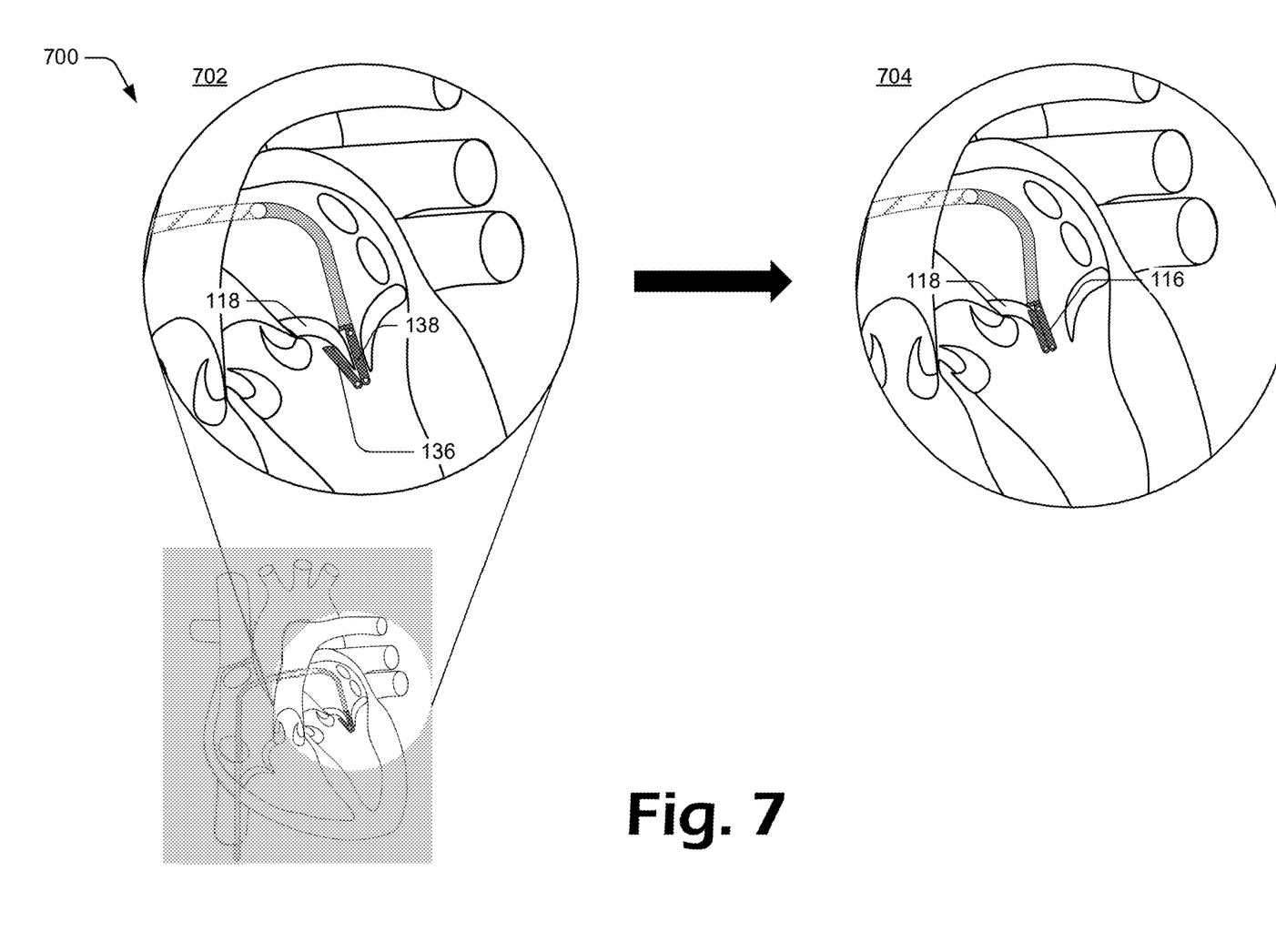
FIG. 7 depicts an example in which the cutting grasper closes into a closed position with the anterior leaflet disposed between the base and actuating members.

FIG. 7 depicts an example 700 in which the cutting grasper 116 grasps the anterior leaflet 118 and closes into the closed position 202. This grasping is depicted in detail in the illustrated example 700 via a first stage 702 and a second stage 704. The cutting grasper 116 may use one or more grasper closing components to close into the closed position 202. By way of example, grasper closing components may include or otherwise be configured using one or more rare earth magnets and/or a system of wires and pulleys. In one or more implementations, such grasper closing components may be configured with a release mechanism, which is operable to release the actuating member 136 from the base member 138, e.g., returning the cutting grasper 116 to or substantially to the open position 204. In this way, the cutting grasper 116 can be repositioned into different positions so that an alignment of a laceration made using the cutting grasper 116 can be adjusted in real-time (e.g., while the cutting grasper 116 is deployed within the patient) based on the anatomy of the patient.

Figure 8:
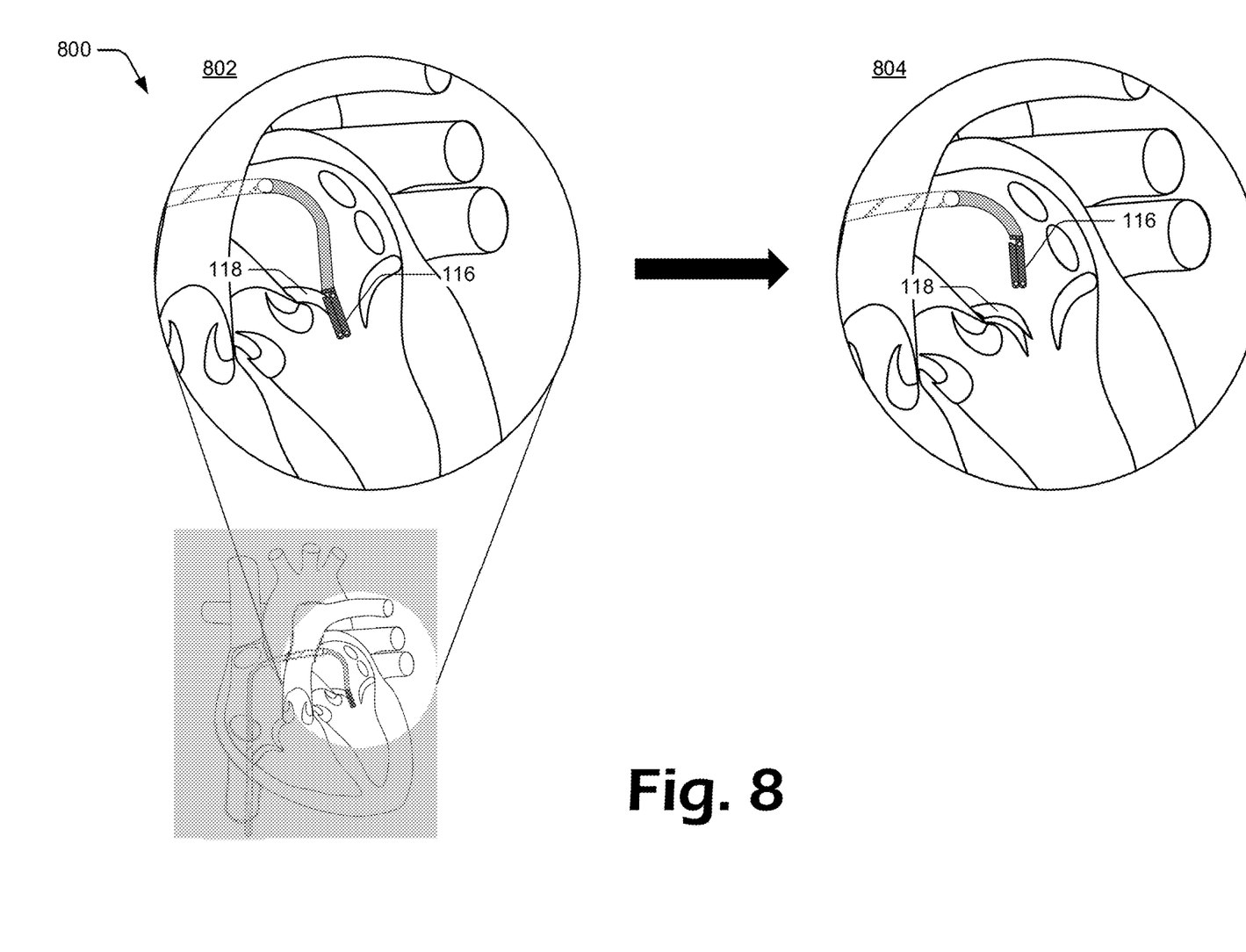
FIG. 8 depicts an example in which the cutting grasper cuts the anterior leaflet and retracts into the left atrium.

FIG. 8 depicts an example 800 in which the cutting grasper 116 lacerates the anterior leaflet 118 and then, while in the closed position 202, retracts through the mitral valve 132 into the left atrium 130. This laceration and retraction are depicted in more detail in the illustrated example 800 via a first stage 802 and a second stage 804.

To divide the anterior leaflet 118, the cutting grasper 116 may use one or more lacerating components. By way of example, such lacerating components may include an electrified wire, one or more magnets, and/or one or more blades, to name just a few. It is to be appreciated that the lacerating components may be configured to lacerate bodily tissue using different materials and or mechanisms without departing from the spirit or scope of the described techniques.

Further, such lacerating components may be disposed on or otherwise included as part of either or both the base member 138 and the actuating member 136. In one or more implementations, the lacerating components may be configured to remain idle until the target tissue (e.g., the anterior leaflet 118) is securely grasped by the cutting grasper 116. In this way, the cutting grasper 116 can mitigate the likelihood of inadvertently damaging healthy tissue. With the anterior leaflet 118 successfully bisected using the cutting grasper 116, as depicted in the second stage 804, the heart 102 is considered surgically "ready" for mitral valve replacement such that a risk of LVOT obstruction is reduced or eliminated.

Figure 9:
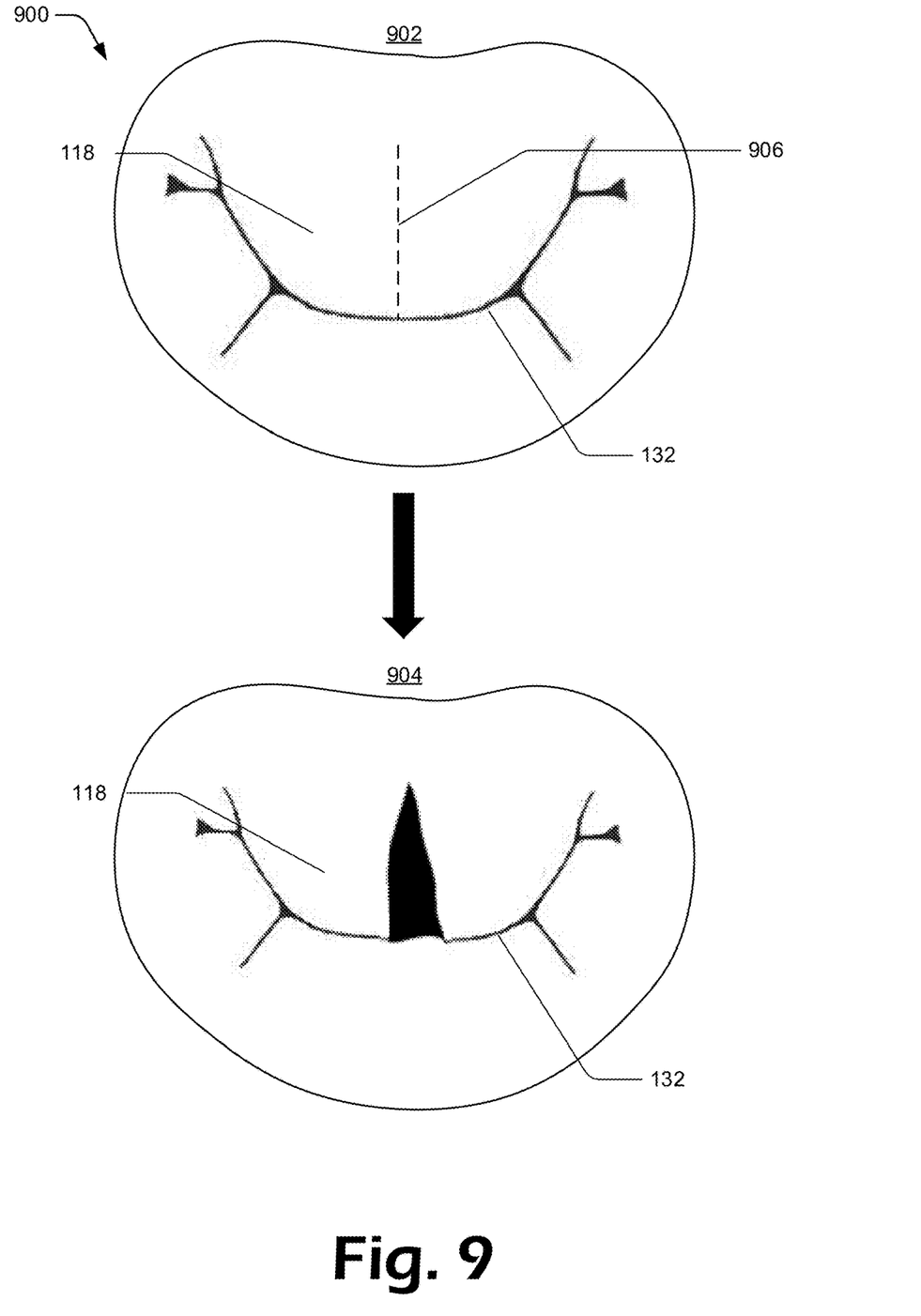
FIG. 9 depicts example posterior views of the mitral valve including the mitral valve before and after laceration by the cutting grasper.

FIG. 9 illustrates example posterior views at 900 of the mitral valve 132, i.e., as if looking down at the mitral valve 132 from the left atrium 130. The mitral valve 132 is shown before being divided 902 as well as after being divided 904. An optimal cut site 906 is also depicted, located on the anterior leaflet 118. The cutting grasper 116 is configured so that the actuating member 136 and the base member 138 may be disposed above and below the optimal cut site 906. Grasper closing components may then be actuated to grasp the target leaflet along the optimal cut site 906. The grasper closing components may also be configured with a release mechanism which is operable to release the actuating member 136 from the base member 138. In this way, the cutting grasper 116 can be repositioned into a different orientation, including along the optimal cut site 906 if the target tissue is not grasped along the optimal cut site 906. This helps overcome limitations of conventional techniques. For instance, the alignment of a laceration made using the LAMPOON procedure may be limited to a single plane which may not be optimal depending on specific anatomy of an individual patient.

With the cutting grasper 116 oriented along the optimal cut site 906, lacerating components of the cutting grasper 116 may then cut the anterior leaflet 118. Due to its ability to release tissue and be repositioned, use of the cutting grasper 116 mitigates the likelihood of inadvertently damaging healthy tissue and ensures that a cut is made only once the lacerating components are aligned with the optimal cut site 906. The resulting cut is shown at 904, with the anterior leaflet 118 bisected along the optimal cut site 906. Lacerating the anterior leaflet 118 along the optimal cut site 906 mitigates the risk of LVOT obstruction upon subsequent mitral valve replacement.

Figure 10:
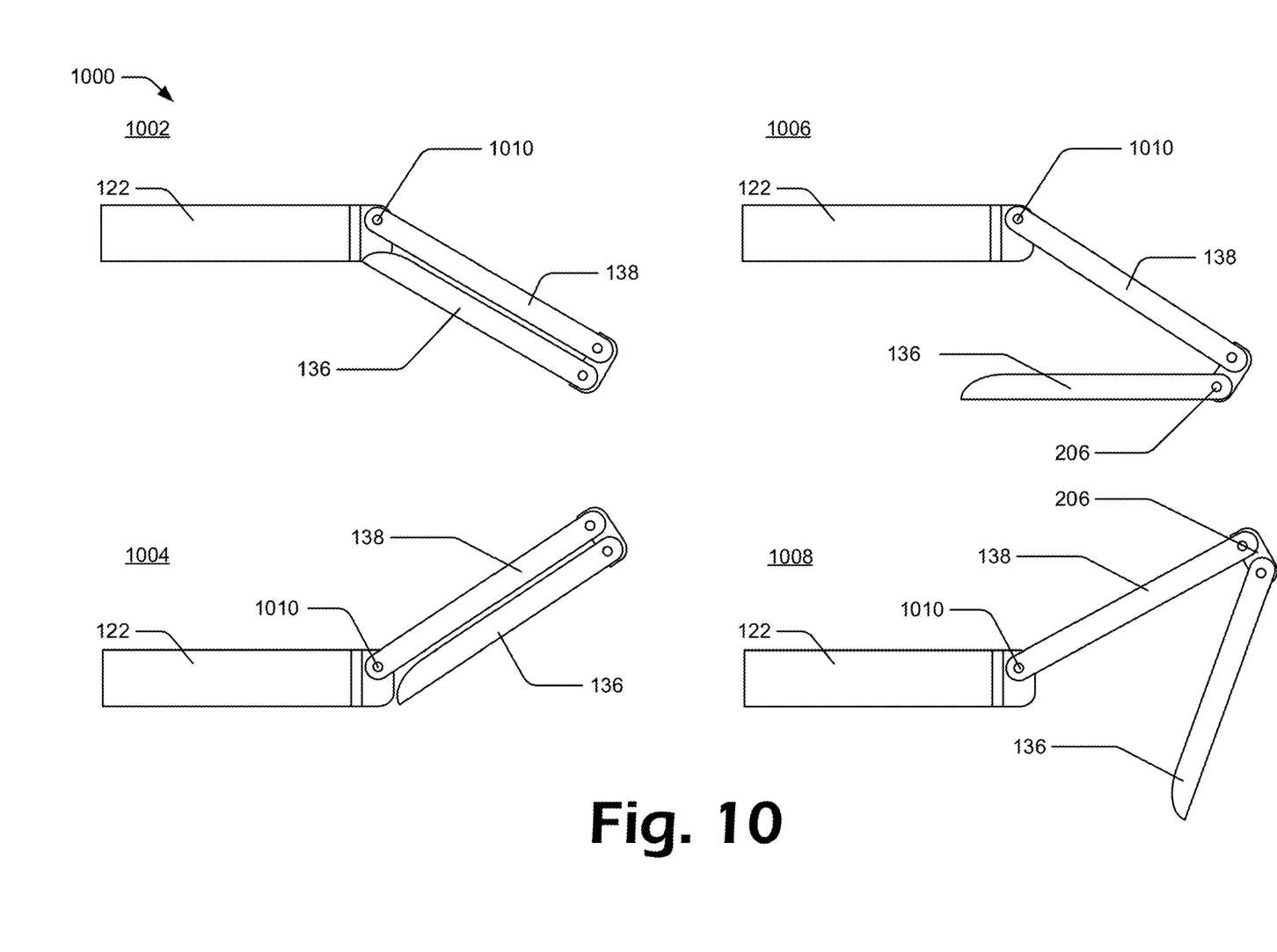
FIG. 10 depicts example implementations in which the cutting grasper is configured to rotate about a base hinge.

FIG. 10 illustrates an examples 1000 in which the cutting grasper is configured to rotate at a base hinge.

Here, the cutting grasper 116 is depicted in four different orientations 1002-1008 and further includes a base hinge 1010. In one or more implementations, the junction of the base member 138 and the flexible shaft 122 forms the base hinge 1010 of the cutting grasper 116. In such implementations, the base member 138 is configured to rotate relative to the flexible shaft 122 about the base hinge 1010 in a first direction and/or a second direction. In the first orientation 1002, for instance, the cutting grasper 116 is in a closed position 202, i.e., the base member 138 and the actuating member 136 are disposed together. In the first orientation 1002, the base member 138 is also illustrated rotated about the base hinge 1010 in a first direction. As depicted in the second orientation 1004, the cutting grasper 116 is also deployed in the closed position 202, but the base member 138 is depicted rotated about the base hinge 1010 in a second direction that is opposite the above-mentioned first direction.

In the third orientation 1006, the cutting grasper 116 is depicted in the open position 204 and the base member 138 is rotated about the base hinge 1010 in the first direction. By way of contrast, in the fourth orientation 1008 the cutting grasper 116 is depicted in the open position 204 and the base member is depicted rotated about the base hinge 1010 in the second direction. In one or more implementations, the cutting grasper 116 can be configured to rotate about the base hinge 1010 automatically. Alternately or in addition, the cutting grasper 116 can be controlled to rotate about the base hinge 1010 by a user of the device, e.g., a surgeon. In this way, the cutting grasper 116 enables a surgeon (or a robot) to have more control generally and finer control over the position and orientation of the device, which overcomes limitations of conventional techniques that involve complicated deployment of medical devices, such as the deployment of two separate catheters as part of performing the LAMPOON technique.

Figure 11:
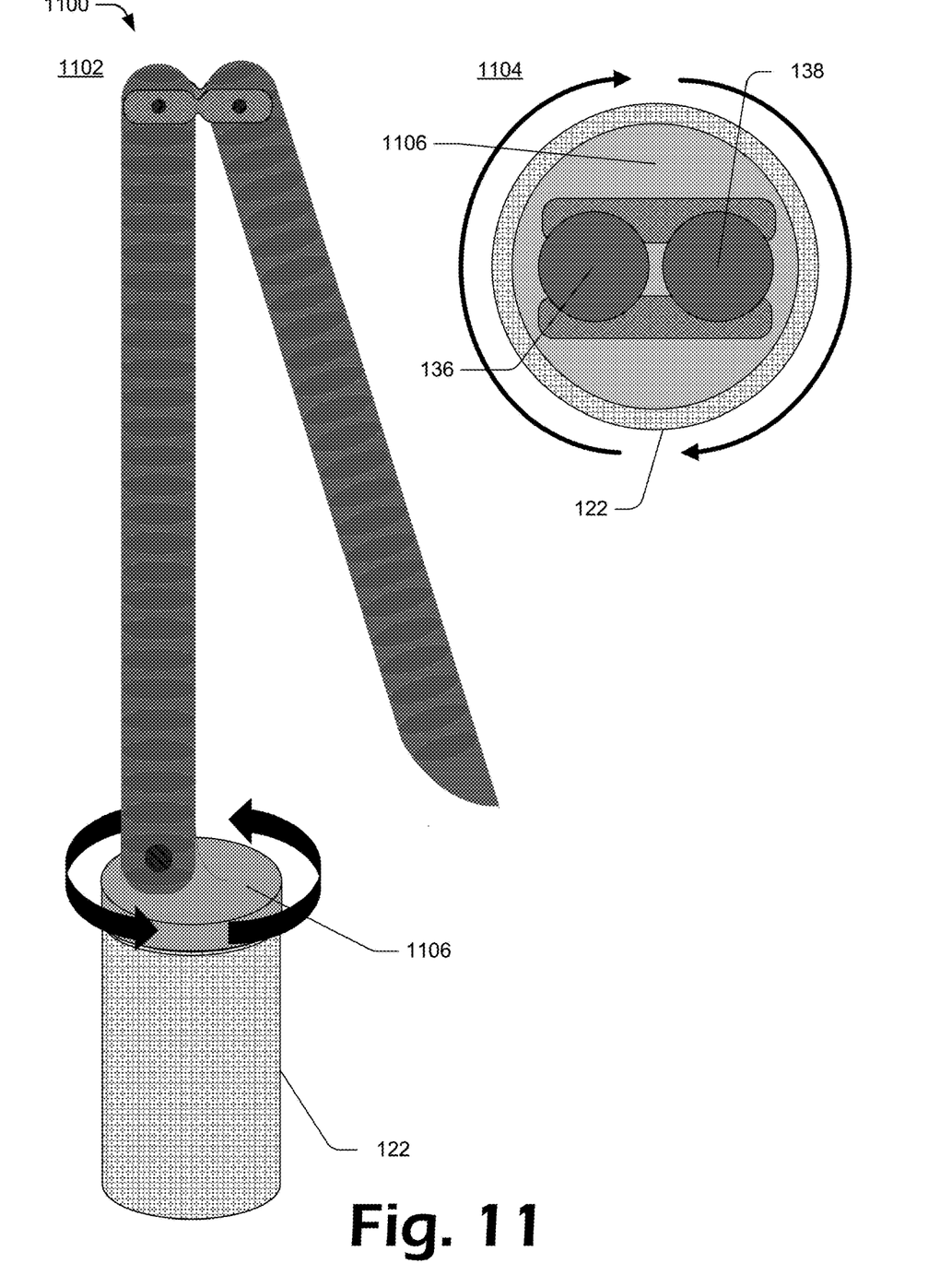
FIG. 11 depicts an example implementation in which the cutting grasper is configured to circumvolve about a rotational component.

FIG. 11 depicts an example 1100 of an implementation in which the cutting grasper 116 is configured to circumvolve about a rotational component.

This example 1100 includes a side view 1102 of the cutting grasper 116 as well as a second view 1104, which looks down on a superior end of the cutting grasper 116. In this example 1100, the cutting grasper 116 is configured to circumvolve about a rotational component 1106. In one or more implementations, the cutting grasper 116 is configured with the rotational component 1106. By way of example and not limitation, the rotational component 1106 is disposed between the distal end of the flexible shaft 122 and the proximal end of the base member 138. In this way, the cutting grasper 116 is configured to circumvolve, clockwise or counterclockwise, substantially about a longitudinal axis that runs substantially through the flexible shaft 122. In one or more implementations, the rotational component can be controlled to cause the cutting grasper 116 to rotate so that it circumvolves substantially about the longitudinal axis. Additionally, the rotational component can be controlled by a user of the device, e.g., a surgeon, to enable the cutting grasper 116 to circumvolve the axis in this way. Advantageously, a user of the device has enhanced control over the position and orientation of the cutting grasper 116, which allows the user to more effectively direct the cutting grasper 116 through the vasculature and position the cutting grasper 116 along an optimal cut site 906.

CONCLUSION

Although the systems and techniques have been described in language specific to structural features and/or methodological acts, it is to be understood that the systems and techniques defined in the appended claims are not necessarily limited to the specific features or acts described. Rather, the specific features and acts are disclosed as example forms of implementing the claimed subject matter.

What is claimed is:

1. A device comprising:
   a flexible shaft having shaft proximal and distal ends; and
   a cutting grasper that extends from the shaft distal end so that the flexible shaft is configured to advance the cutting grasper through a vascular system of a patient and into a chamber of a patient's heart via a valve having a target leaflet, the cutting grasper including:
      a base member having base proximal and distal ends, the base proximal end rotatably attached to the shaft distal end forming a base hinge of the cutting grasper, the base member configured to rotate relative to the flexible shaft about the base hinge; and
      an actuating member having actuating proximal and distal ends, the actuating proximal end located distal from the base proximal end and rotatably attached at the base distal end forming a hinge of the cutting grasper, the actuating member configured to rotate relative to the base member about the hinge between open and closed positions of the cutting grasper, the cutting grasper configured to grasp the target leaflet in the open position, close into the closed position with the target leaflet secured between the base member and the actuating member, and divide the target leaflet while the cutting grasper is in the closed position with the target leaflet secured between the base member and the actuating member.

2. The device of claim 1, further comprising a controller coupled to the shaft proximal end, the controller configured to control the actuating member to rotate from the open position to the closed position.

3. The device of claim 1, further comprising a controller coupled to the shaft proximal end, the controller configured to control the actuating member to rotate from the closed position to the open position.

4. The device of claim 1, further comprising a controller coupled to the shaft proximal end, the controller configured to control the cutting grasper to grasp the target leaflet.

5. The device of claim 1, further comprising a controller coupled to the shaft proximal end, the controller configured to actuate one or more lacerating components to divide the target leaflet while disposed between the base member and the actuating member.

6. The device of claim 1, further comprising one or more grasper closing components including a system of wires and pulleys, the one or more grasper closing components configured to close the cutting grasper into the closed position and secure the target leaflet between the base member and the actuating member.

7. The device of claim 6, wherein the one or more grasper closing components further include one or more magnets.

8. The device of claim 1 wherein the actuating member is configured to rotate into the open position automatically responsive to entry of the cutting grasper into the chamber of the patient's heart.

9. The device of claim 1 wherein the flexible shaft is a catheterized flexible shaft configured to advance the cutting grasper through the vascular system in an antegrade direction.

10. The device of claim 1, wherein the cutting grasper further includes an anchor component rotatably attached to the hinge of the cutting grasper, the anchor component configured to rotate relative to the base member about the hinge and bind to the actuating member to secure the target leaflet between the base member and the actuating member.

11. The device of claim 1, wherein the cutting grasper further includes a rotational component disposed between the shaft distal end and the base proximal end, and wherein the cutting grasper is configured to circumvolve via the rotational component about a longitudinal axis of the flexible shaft.

12. A cutting grasper comprising:
   a base member having base proximal and distal ends, the base proximal end rotatably attached to a flexible shaft forming a base hinge of the cutting grasper, the base member configured to rotate relative to the flexible shaft about the base hinge; and
   an actuating member having actuating proximal and distal ends, the actuating proximal end located distal from the base proximal end and rotatably attached at the base distal end forming a hinge of the cutting grasper, the actuating member configured to rotate relative to the base member about the hinge between open and closed positions of the cutting grasper, the cutting grasper configured to grasp a target leaflet in the open position, close into the closed position with the target leaflet disposed between the base member and the actuating member, and divide the target leaflet while the cutting grasper is in the closed position with the target leaflet secured between the base member and the actuating member.

13. The cutting grasper of claim 12, wherein the flexible shaft is a catheterized flexible shaft configured to advance the cutting grasper through a vascular system of a patient and into a chamber of a patient's heart having the target leaflet.

14. The cutting grasper of claim 12, wherein the base member includes a rotational component, and the cutting grasper is configured to circumvolve about a longitudinal axis of the base member via the rotational component.

* * * * *